United States Patent [19]

Giordano et al.

[11] Patent Number: 5,312,975
[45] Date of Patent: May 17, 1994

[54] PROCESS FOR THE PREPARATION OF 5-(2,4-DIFLUOROPHENYL)-SALICYLIC ACID

[75] Inventors: Claudio Giordano, Monza; Laura Coppi, Florence; Francesco Minisci, Milan, all of Italy

[73] Assignee: Zambon Group S.p.A., Vicenza, Italy

[21] Appl. No.: 813,661

[22] Filed: Dec. 27, 1991

[30] Foreign Application Priority Data

Jan. 8, 1991 [IT] Italy ............................ MI91 A 00027
Apr. 19, 1991 [IT] Italy ......................... MI91 A 001094

[51] Int. Cl.$^5$ .................... C07C 51/15; C07C 41/24; C07C 41/01
[52] U.S. Cl. .................... 562/406; 562/418; 562/423; 562/469; 562/492; 562/477; 562/474; 562/475; 568/637; 568/638; 568/639; 568/642; 568/643; 568/746; 560/141; 548/215
[58] Field of Search ............ 562/492, 477, 407, 408, 562/474, 475, 406, 418, 423, 469; 568/642, 643, 637, 638, 639, 746; 560/141; 548/215

[56] References Cited

U.S. PATENT DOCUMENTS 3,992,459 11/1976 Utne et al. ..................... 568/642
4,225,730 9/1980 Jones et al. .................... 562/469
4,486,599 12/1984 Meneghin et al. ............... 562/469

FOREIGN PATENT DOCUMENTS 1175212 12/1969 European Pat. Off. .
0366573 5/1990 European Pat. Off. .

OTHER PUBLICATIONS

Journal of Organic Chemistry, Chemical Communications, vol. 42, No. 10, 1977, pp. 1821–1823, S. Danishefsky, et al., "Selective Carbon-Carbon Bond Formation via Transition Metal Catalysis.3.$^1$, A Highly Selective Synthesis of Unsymmetrical Biaryls and Diarylmethanes By the Nickel- Or Palladium-Catallyzed Reaction of Aryl-and Benzylzinc Derivatives With Aryl Halides".

Organic Syntheses, vol. 66, 1988, pp. 67–74, E. Negishi, et al., "Synthesis of Biaryls via Palladium-Catalyzed Cross Coupling: 2-Methyl-4'-Nitrobiphenyl (1,1'-Biphenyl", 2-methyl-4'-nitro-).

J. March, Advanced Organic Chemistry—Reactions, Mechanisms, and Structure, 3rd ed., John Wiley & Sons, Inc., U.S.: 1985, p. 425.

The Merck Index, ed. 11, Merck & Co., Inc., New Jersey, U.S.: 1989, p. 3131, No. 3130, "Difllunisal".

The Merck Index, ed. 11, Merck & Co., Inc., New Jersey, U.S.: 1989, pp. 4879, No. 4878, "Infusorial Earth".

*Primary Examiner*—Marianne M. Cintins
*Assistant Examiner*—Margaret J. Page
*Attorney, Agent, or Firm*—Oblon, Spivak, McClelland, Maier & Neustadt

[57] ABSTRACT

A process for the preparation of 5-(2,4-difluorophenyl)-salicylic acid comprising the reaction of an organometallic derivative with a suitable substituted benzene in the presence of a transition-metal based catalyst is described.

12 Claims, No Drawings

PROCESS FOR THE PREPARATION OF 5-(2,4-DIFLUOROPHENYL)-SALICYLIC ACID

The present invention relates to a process for the preparation of 5-(2,4-difluorophenyl)-salicylic acid by cross-coupling reaction. 5-(2,4-difluorophenyl)-salicyclic acid (Merck Index, XI ed., No. 3130, page 495), hereinafter indicated to as compound I, is a drug with anti-inflammatory activity known under the international non-proprietary name (INN) Diflunisal.

In British patent No. 1,175,212 (Merck & Co.), compound I is prepared by Gomberg reaction between a diazonium salt of 2,4-difluoroaniline and anisole, subsequent hydrolysis of the ether group and carboxylation.

However, this method provides compound I in a very low yield because of the formation of by-products which can be difficultly separated. The reason for that is known and it is the fact that Gomberg reaction is not regioselective and, in the specific case of the reaction with anisole, gives a mixture of the three positional ortho, meta and para isomers in which the desired compound (para-isomer) is not the main one.

Furthermore, it is known that Gomberg reaction requires a large excess of substrate (anisole) which is consequently used as a solvent.

Therefore, to our knowledge it is clear that the method for the preparation of compound I described in British patent No. 1,175,212 has no industrial applicability.

In order to overcome these inconveniences, other methods for the preparation of compound I comprising the Gomberg reaction with benzene, which does not cause regioselectivity problems, have been studied.

In fact, as far as we know, the only industrial method for the preparation of compound I is described in U.S. Pat. No. 4,225,730 (Merck & Co.) and comprises the preparation of 2,4-difluoro-biphenyl, the Friedel-Crafts acylation with an acyl derivative of a $C_2$-$C_5$ aliphatic carboxylic acid in order to obtain a 2,4-difluoro-biphenyl 4'-substituted by a $C_2$-$C_5$ alkylcarbonyl group, the oxidation of this compound in order to obtain a 2,4-difluoro-biphenyl 4'-substituted by a $C_2$-$C_5$ alkylcarbonyloxy group, the hydrolysis in order to obtain 4-(2,4-difluorophenyl)-phenol and the carboxylation of this latter in order to obtain compound I.

It can be easily noted that, by carrying out the Gomberg reaction with benzene, the resultant 2,4-difluorobiphenyl must be functionalized in order to obtain compound I.

The need to functionalize the biphenyl molecule leads to a relevant increase in the number of synthetic steps.

It is also known from time in the literature that unsymmetrical biphenyls can be prepared by reaction between an organometallic compound and a haloaryl compound in the presence of metal catalysts such as, for example, palladium and nickel (Org. Synth., 66, 67-74). As far as we know such a method, in spite of its high versatility, has been never used either for the difluoroarylation of phenols or derivatives thereof or, more particularly, for the preparation of compound I.

We have now found, and it is an object of the present invention, a process for the preparation of compound I comprising the reaction between an organometallic derivative of formula $$Ar_1-Q \quad (II)$$

and a compound of formula $$Ar_2-Y \quad (III)$$

wherein

Q is a copper atom or an $MX_n$ group wherein M is a metal selected among magnesium, zinc, cadmium, mercury, boron and aluminum and, when M is magnesium, zinc, cadmium or mercury, X is a chlorine, bromine or iodine atom and n is 1; when M is boron, X is a chlorine, bromine or iodine atom, a hydroxy or a $C_1$-$C_3$ alkoxy and n is 2; when M is aluminum, X is a $C_1$-$C_4$ alkyl and n is 2;

Y is a chlorine, bromine or iodine atom or a trifluoromethanesulfonyloxy group;

$Ar_1$ and $Ar_2$, different from each other, are a difluorophenyl group of formula

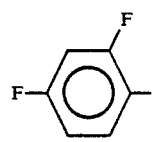

or a phenol derivative of formula

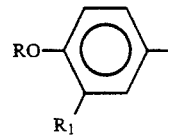

wherein R is a hydrogen atom, a linear or branched $C_1$-$C_5$ alkyl or an optionally substituted phenyl or benzyl; $R_1$ is a hydrogen atom, a carboxyl group or carboxyl precursor group;

in the presence of a transition-metal(O)based catalyst;

in order to obtain a biphenylderivative of formula

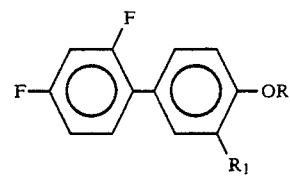

(IV)

wherein R and $R_1$ have the above reported meanings;

the optional hydrolysis of the ether group and the optional carboxylation or transformation of $R_1$ into a carboxyl group.

Preferred examples of transition-metal(O)based catalysts are palladium or nickel, optionally supported, in the presence of ligands such as triphenylphosphine; the transition-metal(O)based catalysts can be optionally prepared in situ starting from their salts such as, for example, nickel chloride, cobalt chloride, nickel acetylacetonate, ferric chloride, palladium chloride, lithium tetrachlorocuprate ($Li_2CuCl_4$), palladium acetate and palladium acetylacetonate. Exclusively for practical reasons, palladium tetrakis(triphenylphosphine), nickel tetrakis(triphenylphosphine) or palladium on charcoal in the presence of triphenylphosphine, optionally prepared in situ according, for example, to the method described in Org. Synth., 66, 67-74, are preferred.

Specific examples of carboxyl precursor groups in the meanings of $R_1$ are methyl, hydroxymethyl, optionally protected as ether, formyl or acetyl, optionally protected as acetals or ketals, from which the carboxyl group can be obtained by oxidation; salts or esters, such as for example t.butylester, of the carboxyl group from which the free carboxyl group can be obtained by hydrolysis or Meyers oxazolines (J. March—Advanced Organic Chemistry—3rd Ed.—John Wiley & Sons Inc., page 425).

The reaction between compound II and compound III is generally carried out in a solvent such as, for example, tetrahydrofuran, diethyl ether, methyl-t.butyl ether, diamyl ether, dibutyl ether, ethylene glycol, dioxane, toluene, benzene, xylene, ethanol or mixtures thereof.

When the compounds of formula II in which M=Boron are used, the reaction is preferably carried out in the presence of a base and in a hydroalcoholic or aqueous medium optionally in a biphasic system constituted by a hydroalcoholic or aqueous medium and by an immiscible organic solvent.

Examples of bases are sodium carbonate, potassium carbonate, sodium bicarbonate, potassium bicarbonate, sodium hydroxide, potassium hydroxide.

The reaction temperature is generally between $-30°$ C. and $80°$ C., preferably between $15°$ C. and $65°$ C.

The molar amount of catalyst is between 0.05% and 2%.

The optional hydrolysis of the ether group (R different from hydrogen) is carried out according to known methods.

When the reaction is carried out by using a compound of formula II wherein $R_1$ is hydrogen, the obtained biphenylderivative of formula IV (R=H) will be carboxylated according to known methods, preferably according to the methods described in U.S. Pat. No. 4,486,599 (Zambon S.p.A.) in order to obtain compound I.

The compounds of formula II wherein M is boron and $Ar_1$ is a difluorophenyl group, hereinafter referred to as compound II-A

(II-A)

are new and they are a further object of the present invention.

The compounds of formula II wherein Q is a copper atom or an $MX_n$ wherein M is different from boron are known or they can be prepared according to known methods.

For example, the magnesium halides (Grignard compounds) of formula II (M=Mg) can be prepared from the corresponding haloderivatives of formula $Ar_1$—Z     (V)

wherein $Ar_1$ has the above reported meanings and Z is a chlorine, bromine or iodine atom; by reaction with magnesium.

The other organometallic compounds of formula II can be prepared according to conventional transmetalation reactions from the corresponding lithium derivatives.

Alternatively, the compounds of formula II-A wherein X is a hydroxy or a $C_1$-$C_3$ alkoxy group can be prepared from the corresponding Grignard compounds (II, M=Mg) by reaction with a suitable borate and optional subsequent hydrolysis.

Exclusively for practical and economic reasons the Grignard compounds of formula II, which can be directly prepared in situ, are preferably used.

The Grignard compounds of formula II wherein $Ar_1$ is a group of formula

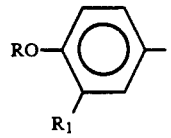

and R is a linear or branched $C_1$-$C_4$ alkyl or a benzyl are particularly preferred.

Another preferred embodiment of the process object of the present invention comprises the transformation of the Grignard compounds of formula II into the corresponding boronic acid derivative of formula II (M=B, X=OH).

Also the compounds of formula III are known or they can be prepared according to known methods.

In a practical embodiment of the process object of the present invention, a Grignard compound of formula II, prepared in situ, is directly added to a solution of a compound of formula III and of a catalyst at a temperature between $15°$ C. and $65°$ C.

When R is different from hydrogen, after hydrolysis of the ether group, for example by treatment with acids, a compound of formula IV wherein R=H is obtained.

From this latter, compound I is prepared by carboxylation when $R_1$=H or by oxidation or hydrolysis, as already described, when $R_1$ is a carboxyl precursor group.

In another practical embodiment of the process object of the invention, a Grignard compound of formula II, prepared in situ, is directly transformed into the corresponding boronic acid derivative of formula II by reaction with a trialkylborate, for example trimethylborate, and by subsequent hydrolsis at a temperature generally between $-20°$ C. and $0°$ C.

The resultant boronic acid derivative is then added to a mixture of a compound of formula III, of a base and of a catalyst in a suitable solvent at a temperature between $15°$ C. and $65°$ C.

After optional hydrolysis of the ether group, for example by treatment with acids, a compound of formula IV wherein R=H is obtained. From this latter, compound I is prepared by carboxylation when $R_1$=H or by oxidation or hydrolysis, as already described, when $R_1$ is a carboxyl precursor group.

The main advantage of the process object of the present invention consists in the fact that it allows to obtain compound I by a simple cross-coupling reaction of already functionalized aryl derivatives, with few steps and in very high yields.

This advantage is due to the fact that the reaction between compound II and compound III according to the invention is extremely regio-selective giving exclusively the desired isomer of formula IV. Furthermore, the use of already functionalized starting compounds does not require to further functionalize the biphenyl molecule with a consequent decrease in the number of synthetic steps.

Another advantage of the process of the invention is that the catalyst is used in very small amounts while keeping mild reaction conditions and high yields.

A further advantage of the process object of the invention, which is worth noting, is the easy availability at low costs of the starting compounds.

Finally, it is clear to one skilled in the art how the process of the invention is particularly suitable for the industrial application.

In order to better illustrate the present invention the following examples are now given.

EXAMPLE 1

Preparation of 4-(2,4-difluorophenyl)-anisole from 4-methoxyphenyl-magnesiumbromide and palladium tetrakis(triphenylphosphine) (2%)

An iodine crystal and, then, some drops of a solution of 4-bromoanisole (8.1 g; 43.34 mmoles) in tetrahydrofuran (31 ml) were added to a suspension of magnesium turnings (1.1 g; 45.5 mmoles—Aldrich) in tetrahydrofuran (6 ml).

The mixture was heated up to the beginning of the Grignard reaction. Then, the solution of 4-bromoanisole was added dropwise so as to keep the reaction mixture under reflux.

At the end of the addition, the mixture was kept under reflux for further 30 minutes (solution A).

Palladium tetrakis(triphenylphosphine) (1 g; 0.866 mmoles), prepared from $PdCl_2$ (Fluka) and triphenylphosphine (Fluka), was added to a solution of 1-bromo-2,4-difluorobenzene (8.36 g; 43.34 mmoles) in tetrahydrofuran (43.5 ml), de-aerated by vacuum/nitrogen, and the solution was kept under stirring at 20° C. for 15 minutes (solution B).

Solution A was added to solution B and, then, the mixture was heated to reflux. After 1 hour, the reaction mixture was cooled at 20° C. and poured into 1N hydrochloric acid (170 ml). After addition of ethyl ether (170 ml), the phases were separated and the organic phase was washed with 1N hydrochloric acid (170 ml), 8% sodium bicarbonate (170 ml) and water (170 ml).

After dryness and evaporation of the solvent, the resultant crude (11 g) was purified by column chromatography (silica gel, benzene:n.hexane=1:2) obtaining the desired compound (8.1 g; 80% yield).

Similar results were obtained by using a 0.2% amount of catalyst.

EXAMPLE 2

Preparation of 4-(2,4-difluorophenyl)-phenol.

To a 33% solution of hydrobromic acid in acetic acid (1.5 ml) 4-(2,4-difluorophenyl)-anisole (0.22 g; 1 mmole), prepared as described in example 1, was added.

The mixture was kept under stirring under nitrogen at 50° C. for 66 hours. Then, the reaction mixture was evaporated to dryness under reduced pressure and the resultant residue was recovered with a mixture water-:ethyl ether=1:1 (5 ml).

The ethereal phase was separated and washed with aqueous sodium bicarbonate and, then, dried on sodium sulfate.

After removing the solvent under reduced pressure, the resultant crude (0.17 g) was purified by column chromatography (silica gel, n.hexane:ethyl ether=7:3) obtaining the pure compound (0.15 g). $^1$H-NMR (300 MHz, $CDCl_3$) δ (ppm): 4.9 (s, 1H); 6.85-7.42 (m, 7H).

EXAMPLE 3

Preparation of 5-(2,4-difluorophenyl)-salicylic acid $CO_2$ was bubbled into a solution of sodium methoxide, obtained by dissolving sodium (4.46 g; 0.19 moles) in methanol (100 ml), at 20° C. up to complete conversion of methoxide into sodium methylcarbonate. 4-(2,4-difluorophenyl)-phenol (20 g; 0.097 moles), prepared as described in example 2, was added to the resultant suspension.

The solvent was evaporated, recovering methanol (92 ml), up to a temperature of 120°-130° C. (external bath).

The reaction mixture was kept under nitrogen and the temperature of the external bath was gradually increased up to 200° C. and kept under these conditions for 8 hours.

After cooling, the reaction crude was dissolved in boiling water (800 ml).

After filtration and neutralization at pH 7 with concentrated HCl (10 ml), $K_2CO_3$ (10 g) was added to the solution.

The resultant solution was extracted at warm (80° C.) with 1,1,2-trichloroethylene (3×100 ml). From the collected organic extracts, after evaporation of the solvent under reduced pressure, 4-(2,4-difluorophenyl)-phenol (1.6 g; 0.008 moles) was obtained.

The aqueous phase, kept at 80° C., was added dropwise to a 15% solution of hydrochloric acid (200 ml) under stirring.

The resultant suspension was extracted at room temperature with ethyl ether (300 ml) and the organic phase was separated, dried and evaporated to obtain 5-(2,4-diflurophenyl)-salicylic acid (21.8 g; 0.087 moles; 98% yield).

EXAMPLE 4

Preparation of 4-(2,4-difluorophenyl)-anisole from 4-methoxyphenylmagnesium bromide and palladium tetrakis(triphenylphosphine) (0.5%)

A suspension of magnesium turnings (1.53 g; 63.6 mmoles-Aldrich) in tetrahydrofuran (25 ml) was heated to the reflux temperature under stirring and under nitrogen, and then iodine (20 mg) was added.

After decolorization of iodine, a solution of 4-bromoanisole (11.2 g; 60 mmoles) in tetrahydrofuran (10 ml) was added dropwise in 1 hour to the suspension under stirring.

At the end of the addition, the suspension was kept under reflux for 30 minutes, then cooled at 20° C. and filtered.

A solution of 4-methoxyphenylmagnesiumbromide was obtained (solution A).

Palladium tetrakis(triphenylphosphine) (0.23 g; 0.2 mmoles), prepared from $PdCl_2$ (Fluka) and triphenylphosphine (Fluka), was added, under nitrogen, to a solution of 1-bromo-2,4-difluorobenzene (7.72 g; 40 mmoles) in tetrahydrofuran (5 ml).

The resultant solution was heated under reflux and then solution A was added in 16 hours.

At the end of the addition, the reaction mixture was kept under reflux for 3 hours, cooled at 20° C. and, then, poured into water (100 ml) containing 36% hydrochloric acid (5 ml).

The phases were separated and the aqueous phase was extracted with methylene chloride (20 ml).

The collected organic phases were evaporated under reduced pressure and the resultant residue (12 g) was purified by column chromatography (silica gel, toluene:n.hexane=6.4) obtaining the desired compound (8.2 g; HPLC titre 91%; 85% yield).

EXAMPLE 5

Preparation of 4-(2,4-difluorophenyl)-anisole from 4-methoxyphenylboronic acid and palladium tetrakis(triphenylphosphine) (2%)

A hot solution (60° C.) of 4-methoxyphenylboronic acid (5.32 g; 35 mmoles) in ethanol (14 g) was added to a mixture of palladium tetrakis(triphenylphosphine) (0.81 g; 0.7 mmoles), prepared from $PdCl_2$ (Fluka) and triphenylphosphine (Fluka), benzene (56 g), 1-bromo-2,4-difluorobenzene (6.18 g; 32 mmoles) and a 2M aqueous sodium bicarbonate solution (35 g), kept under stirring and under nitrogen at 20° C.

The reaction mixture was heated under reflux and under stirring for 5 hours.

After cooling to 20° C. in 1 hour, the reaction mixture was poured into a mixture of methylene chloride (100 g) and water (50 g).

The organic phase was evaporated to dryness under reduced pressure obtaining the desired compound (8.30 g; HPLC titre 75%; 81% yield).

EXAMPLE 6

Preparation of 4-(2,4-difluorophenyl)-anisole from 4-methoxyphenylboronic acid and palladium tetrakis(triphenylphosphine) (0.5%)

The procedure described in example 5 was repeated by using a 0.5% concentration of palladium tetrakis(triphenylphosphine) and adding 4-methoxyphenylboronic acid and ethanol at cold.

The desired compound was obtained with HPLC titre 90.63% and 98% yield.

EXAMPLE 7

Preparation of 4-(2,4-difluorophenyl)-anisole from 4-methoxyphenylmagnesium bromide and nickel acetylacetonate (2%)

A suspension of magnesium turnings (0.62 g; 25.7 mmoles-Aldrich) in dry tetrahydrofuran (19 ml) was heated to the reflux temperature under nitrogen and, then, iodine (30 mg) was added.

After decolorization of iodine, 4-bromoanisole (4.00 g; 21.4 mmoles) was added, in 40 minutes, to the suspension.

At the end of the addition, the reaction mixture was kept under reflux for 90 minutes, let coal up to room temperature and filtered under nitrogen on celite (Merck Index, XI ed., No. 4878, page 787).

A solution of 4-methoxyphenylmagnesiumbromide was obtained (solution A).

Solution A was added dropwise in 45 minutes to a mixture of 1-bromo-2,4-difluorobenzene (4.13 g; 21.4 mmoles) and nickel acetylacetonate (0.11 g; 0.43 mmoles-Aldrich) in dry tetrahydrofuran (20 ml) cooled at −20° C.

The reaction mixture was kept at −20° C. under stirring and under nitrogen for 24 hours and, then, poured into 1N hydrochloric acid (50 ml). Methylene chloride (25 ml) was added.

After filtration on celite (Merck Index, XI ed., No. 4878, page 787) and separation of the phases, the aqueous phase was extracted again with methylene chloride.

The collected organic phases were washed with water (15 ml) and dried.

After evaporation of the solvent, the resultant crude (5.32 g) was purified by column chromatography (silica gel, benzene:n.hexane=1:2) obtaining the desired compound (2.38 g; 50.5% yield).

EXAMPLE 8

Preparation of 4-(2,4-difluorophenyl)-anisole from 4-methoxyphenylzinc chloride and palladium tetrakis(triphenylphosphine) (2%)

A 1.7M solution of t.butyllithium (Aldrich) in pentane (11.8 ml) was added to a solution of 4-bromoanisole (1.87 g; 10 mmoles) in dry tetrahydrofuran (10 ml), cooled at −70° C., while keeping the temperature between −70° C. and −65° C.

A solution of zinc chloride (2.04 g; 15 mmoles-Aldrich) in dry tetrahydrofuran (20 ml) was added, at −70° C., to the resultant solution.

At the end of the addition, the temperature was let arise up to 15° C. spontaneously.

The solution was filtered and added dropwise to a solution of 1-bromo-2,4-difluorobenzene (1.93 g; 10 mmoles) and palladium tetrakis(triphenylphosphine) (0.23 g; 0.2 mmoles), prepared from $PdCl_2$ (Fluka) and triphenylphosphine (Fluka), in tetrahydrofuran (10 ml), at 60° C. in 1 hour.

After 20 hours the reaction mixture was poured into 1N hydrochloric acid (15 ml) and methylene chloride (10 ml) was added.

After separation of the phases, the organic phase was washed with water (5 ml), dried and evaporated to dryness under reduced pressure. The resultant crude was purified by column chromatography (silica gel, n.hexane:benzene=2:1) obtaining the desired compound (1.19 g; 54% yield).

EXAMPLE 9

Preparation of 4-(2,4-difluorophenyl)-anisole from 4-methoxyphenylmagnesiumbromide and palladium tetrakis(triphenylphosphine) (0.15%)

A suspension of magnesium turnings (0.765 g; 31.8 mmoles-Aldrich) in dry tetrahydrofuran (18 ml) and iodine (0.02 g) was heated under reflux and under nitrogen and 4-bromoanisole (5.61 g; 30 mmoles) was added in 1 hour.

At the end of the addition, the suspension was kept under reflux for 1 hour and then filtered under nitrogen.

A solution of 4-methoxyphenylmagnesiumbromide was obtained (solution A).

A mixture of 1-bromo-2,4-difluorobenzene (3.86 g; 20 mmoles) and palladium tetrakis)triphenylphosphine) (0.035 g; 0.03 mmoles), prepared from $PdCl_2$ (Fluka) and triphenylphosphine (Fluka), in dry tetrahydrofuran (5 ml) was heated under reflux and under nitrogen and, then, solution A was added in 16 hours.

At the end of the addition, the reaction mixture was kept under reflux for 4 hours and, then, poured into 1N hydrochloric acid (50 ml).

The phases were separated and the aqueous phase was extracted with methylene chloride (2×10 ml).

The collected organic phases were evaporated under reduced pressure and the resultant crude (5 g) was purified by column chromatography (silica gel, n:hexane:-benzene=2:1) obtaining the desired compound (3.84 g; 87.5% yield).

EXAMPLE 10

Preparation of 4-(2,4-difluorophenyl)-anisole from 4-methoxyphenylmagnesiumbromide and palladium acetate/triphenylphosphine (2%)

A suspension of magnesium turnings (0.62 g; 25.8 mmoles—Aldrich) in dry tetrahydrofuran (18 ml) and iodine (0.02 g) was heated under reflux and under nitrogen and kept under stirring for 30 minutes. 4-Bromoanisole (4.00 g; 21.4 mmoles) was added dropwise in 40 minutes and the reaction mixture was kept under reflux and stirring for 1.5 hours and, then, filtered at warm under nitrogen.

A solution of 4-methoxyphenylmagnesiumbromide was obtained (solution A).

A mixture of 1-bromo-2,4-difluorobenzene (4.13 g; 21.4 mmoles), palladium acetate (0.096 g; 0.43 mmoles—Janssen) and triphenylphosphine (0.45 g; 1.72 mmoles—Fluka) in dry tetrahydrofuran (15 ml) was heated under reflux and under nitrogen and, then, solution A was added in 2.5 hours.

At the end of the addition, the reaction mixture was kept under stirring and under reflux overnight.

After cooling at room temperature, the mixture was poured into 1N hydrochloric acid (20 ml).

The phases were separated and the aqueous phase was extracted with methylene chloride (15 ml).

The collected organic phases were evaporated under reduced pressure and the resultant crude (4.65 g) was purified by column chromatography (silica gel, n.hexane:benzene=2:1) obtaining the desired compound (3.53 g; 75% yield).

EXAMPLE 11

Preparation of 4-(2,4-difluorophenyl)-anisole from 4-methoxyphenylmagnesiumbromide and palladium acetylacetonate/triphenylphosphine (2%)

A suspension of magnesium turnings (0.62 g; 25.8 mmoles—Aldrich) in dry tetrahydrofuran (18 ml) and iodine (0.02 g) was heated under reflux and under nitrogen and kept under stirring for 30 minutes. 4-Bromoanisole (4.00 g; 21.4 mmoles) was added dropwise in 40 minutes and the reaction mixture was kept under reflux and stirring for 1.5 hours and, then, filtered at warm under nitrogen.

A solution of 4-methoxyphenylmagnesiumbromide was obtained (solution A).

A mixture of 1-bromo-2,4-difluorobenzene (4.13 g; 21.4 mmoles), palladium acetylacetonate (0.13 g; 0.43 mmoles), prepared from $PdCl_2$ (Fluka) and acetylacetone (Aldrich), and triphenylphosphine (0.45 g; 1.72 mmoles—Fluka) in dry tetrahydrofuran (15 ml) was heated under reflux and under nitrogen and, then, solution A was added in 2.5 hours.

At the end of the addition, the reaction mixture was kept under reflux and stirring overnight.

After cooling at room temperature, the mixture was poured into 1N hydrochloric acid (20 ml).

The phases were separated and the aqueous phase was extracted with methylene chloride (15 ml).

The collected organic phases were evaporated under reduced pressure and the resultant crude (4.42 g) was purified by column chromatography (silica gel, n.hexane:benzene=2:1) obtaining the desired compound (2.97 g; 63% yield).

EXAMPLE 12

Preparation of 4-(2,4-difluorophenyl)-anisole from 4-methoxyphenylmagnesiumbromide and palladium acetate/triphenylphosphine (0.5%)

A suspension of magnesium turnings (1.53 g; 62.9 mmoles—Aldrich) in dry tetrahydrofuran (35 ml) and iodine (0.03 g) was heated under reflux and under nitrogen and kept under stirring for 30 minutes. 4-Bromoanisole (11.22 g; 60 mmoles) was added dropwise in 1 hour and the reaction mixture was kept under reflux and stirring for 1.5 hours and, then, filtered at warm under nitrogen.

A solution of 4-methoxyphenylmagnesiumbromide was obtained (solution A).

A mixture of 1-bromo-2,4-difluorobenzene (11.58 g; 60 mmoles), palladium acetate (0.067 g; 0.3 mmoles—Janssen) and triphenylphosphine (0.315 g; 1.2 mmoles—Fluka) in dry tetrahydrofuran (7.5 ml) was heated under reflux and under nitrogen and, then, solution A was added in 16 hours.

At the end of the addition, the reaction mixture was kept under stirring and under reflux for 3 hours.

After cooling at room temperature, the mixture was poured into 1N hydrochloric acid (50 ml).

The phases were separated and the aqueous phase was extracted with methylene chloride (25 ml).

The collected organic phases were evaporated under reduced pressure and the resultant crude (11.45 g) was purified by column chromatography (silica gel, n.hexane:benzene=2:1) obtaining the desired compound (10.70 g; 81% yield).

EXAMPLE 13

Preparation of 4-(2,4-difluorophenyl)-anisole from 4-methoxyphenylmagnesiumbromide and palladium tetrakis(triphenylphosphine) (0.1%)

A suspension of magnesium turnings (268 g; 11.02 moles—Janssen) in tetrahydrofuran (2695 g) was heated at 65° C. under stirring and under nitrogen. Then, iodine (2.7 g) and, after 30 minutes, 4-bromoanisole (2000 g; 10.69 moles), in 1 hour, were added to the reaction mixture.

At the end of the addition, the reaction mixture was kept at 75° C. for 1 hour and, then, decanted obtaining a solution of methoxyphenylmagnesiumbromide (solution A).

1-Bromo-2,4-difluorobenzene (1966 g; 10.18 moles) was heated under nitrogen at 60° C. and then de-aerated by vacuum/nitrogen. Palladium tetrakis(triphenylphosphine) (11.76 g; 0.011 moles), prepared from $PdCl_2$ (Fluka) and triphenylphosphine (Fluka), was added and the mixture was heated at 80° C. Solution A was, then, added in 4.5 hours.

At the end of the addition, the reaction mixture was kept at 80° C. for 30 minutes, cooled at 55° C. and poured into water and ice (2000 g).

After cooling at 30° C., the phases were separated and the solvent of the organic phase was evaporated under reduced pressure. The resultant crude was crystallized from isopropanol obtaining the desired compound (2070 g; HPLC titre 98.30%, 91% yield).

EXAMPLE 14

Preparation of 4-(2,4-difluorophenyl)-anisole from 4-methoxyphenylmagnesiumbromide and palladium tetrakis(triphenylphosphine) (0.1%)

A suspension of magnesium turnings (2.67 g; 110 mmoles—Pometon) in tetrahydrofuran (26.95 g) was heated at 65° C. under stirring and under nitrogen. Then, iodine (0.03 g) and, after 30 minutes, 4-bromoanisole (20 g; 107 mmoles), in 1 hour, were added to the reaction mixture.

At the end of the addition, the reaction mixture was kept at 75° C. for 1 hour and, then, decanted obtaining a solution of 4-methoxyphenylmagnesiumbromide (solution A).

1-Bromo-2,4-difluorobenzene (19.66 g; 102 mmoles) was heated under nitrogen at 60° C. and then de-aerated by vacuum/nitrogen. Palladium tetrakis(triphenylphosphine) (0.12 g; 0.11 mmoles), prepared from $PdCl_2$ (Fluka) and triphenylphosphine (Fluka), was added and the mixture was heated at 80° C. and kept under stirring for 30 minutes. Solution A was, then, added in 4 hours.

At the end of the addition, the reaction mixture was kept at 80° C. for 30 minutes and, then, toluene (30 ml) was added.

After cooling at 55° C., a 1N aqueous solution of hydrochloric acid (20 ml) was added in 10 minutes. The mixture was cooled at 40° C. and the phases were separated.

The solvent of the organic phase was evaporated under reduced pressure obtaining the desired compound (25.26 g; HPLC titre 83.58%; 91% yield).

EXAMPLE 15

Preparation of 4-(2,4-difluorophenyl)-anisole from 4-methoxyphenylmagnesiumbromide and palladium acetate/triphenylphosphine (0.1%)

A suspension of magnesium turnings (5.34 g; 220 mmoles—Pometon) in tetrahydrofuran (54 g) was heated at 65° C. under stirring and under nitrogen. Then, iodine (0.06 g) and, after 30 minutes, 4-bromoanisole (40 g; 214 mmoles), in 1 hour, were added to the reaction mixture.

At the end of the addition, the reaction mixture was kept at 75° C. for 1 hour and, then, decanted obtaining a solution of 4-methoxyphenylmagnesiumbromide (solution A).

A mixture of 1-bromo-2,4-difluorobenzene (39.32 g; 204 mmoles), palladium acetate (0.04559 g; 0.203 mmoles—Janssen) and triphenylphosphine (0.2088 g; 0.796 mmoles—Fluka) was de-aerated by vacuum/nitrogen at 25° C. The mixture was heated at 88° C. and solution A was added in 4 hours.

At the end of the addition, the reaction mixture was kept at 88° C. for 30 minutes and, then, toluene (60 ml) was added.

After cooling at 50° C., a 1N aqueous solution of hydrochloric acid (40 ml) was added in 10 minutes. The mixture was cooled at 40° C. and the phases were separated.

The solvent of the organic phase was evaporated under reduced pressure obtaining the desired compound (45.3 g; HPLC titre 95%; 97% yield).

EXAMPLE 16

Preparation of 4-(2,4-difluorophenyl)-anisole from 4-methoxyphenylmagnesiumbromide and palladium acetate/triphenylphosphine (0.1%)

A suspension of magnesium turnings (13.5 g; 555 mmoles—Janssen) in tetrahydrofuran (132.9 g) was heated at 65° C. under stirring and under nitrogen. Then, iodine (0.35 g) and, after 30 minutes, 4-bromoanisole (102.65 g; 549 mmoles), in 1 hour, were added to the reaction mixture.

At the end of the addition, the reaction mixture was kept at 75° C. for 1 hour and, then, decanted obtaining a solution of 4-methoxyphenylmagnesiumbromide (solution A).

A mixture of 1-bromo-2,4-difluorobenzene (100 g; 518 mmoles), palladium acetate (0.11644 g; 0.519 mmoles—Janssen) and triphenylphosphine (0.54356 g; 2.07 mmoles—Fluka) was de-aerated by vacuum/nitrogen at 25° C. The mixture was heated at 85° C., kept under stirring for 15 minutes and, then, solution A was added in 6 hours.

At the end of the addition, the reaction mixture was kept at 85° C. for 30 minutes.

After cooling at 60° C., a solution of 37% hydrochloric acid (17.5 ml) in water (88 ml) was added in 20 minutes.

The mixture was cooled at 40° C. and the phases were separated.

The solvent of the organic phase was evaporated under reduced pressure obtaining the desired compound (113 g; HPLC titre 93.71%; 93% yield).

EXAMPLE 17

Preparation of 4-(2,4-difluorophenyl)-anisole from 4-methoxyphenylmagnesiumbromide and palladium acetate/triphenylphosphine (0.05%)

A suspension of magnesium turnings (1.54 g; 63.3 mmoles—Pometon) in tetrahydrofuran (16.02 g) was heated at 65° C. under stirring and under nitrogen. Then, iodine (0.02 g) and, after 30 minutes, 4-bromoanisole (11.69 g; 62.5 mmoles), in 1 hour, were added to the reaction mixture.

At the end of the addition, the reaction mixture was kept at 75° C. for 1 hour and, then, decanted obtaining a solution of 4-methoxyphenylmagnesiumbromide (solution A).

A mixture of 1-bromo-2,4-difluorobenzene (11.4 g; 59.1 mmoles), palladium acetate (0.00663 g; 0.0295 mmoles—Janssen) and triphenylphosphine (0.03074 g; 0.1172 mmoles—Fluka) was de-aerated by vacuum/nitrogen at 25° C. The mixture was heated at 85° C., kept under stirring for 15 minutes and, then, solution A was added in 3 hours.

At the end of the addition, the reaction mixture was kept at 85° C. for 30 minutes.

After cooling at 60° C., a solution of 37% hydrochloric acid (2 ml) in water (10 ml) was added in 20 minutes.

The mixture was cooled at 40° C. and the phases were separated.

The solvent of the organic phase was evaporated under reduced pressure obtaining the desired compound (92% yield).

EXAMPLE 18

Preparation of 4-(2,4-difluorophenyl)-anisole from 4-methoxyphenylmagnesiumbromide and palladium chloride/triphenylphosphine (0.1%)

A suspension of magnesium turnings (2.67 g; 110 mmoles—Pometon) in tetrahydrofuran (26.95 g) was heated at 65° C. under stirring and under nitrogen. Then, iodine (0.03 g) and, after 30 minutes, 4-bromoanisole (20 g; 107 mmoles), in 1 hour, were added to the reaction mixture.

At the end of the addition, the reaction mixture was kept at 75° C. for 1 hour and, then, decanted obtaining a solution of 4-methoxyphenylmagnesiumbromide (solution A).

A mixture of 1-bromo-2,4-difluorobenzene (19.66 g; 102 mmoles), palladium chloride (0.01784 g; 0.10 mmoles—Degussa) and triphenylphosphine (0.10492 g; 0.40 mmoles—Fluka) was de-aerated by vacuum/nitrogen. The mixture was heated at 88° C. and solution A was added in 4 hours.

At the end of the addition, the reaction mixture was kept at 88° C. for 30 minutes and, then, toluene (30 ml) was added.

After cooling at 55° C., a 1N aqueous solution of hydrochloric acid (20 ml) was added in 10 minutes.

The mixture was cooled at 40° C. and the phases were separated.

The solvent of the organic phase was evaporated under reduced pressure obtaining the desired compound (25.26 g; HPLC titre 94.5%; 95% yield).

EXAMPLE 19

Preparation of 4-(2,4-difluorophenyl)-anisole from 4-methoxyphenylmagnesiumbromide and palladium chloride/triphenylphosphine (0.05%)

A suspension of magnesium turnings (1.54 g; 63.3 mmoles-Pometon) in tetrahydrofuran (16.02 g) was heated at 65° C. under stirring and under nitrogen. Then, iodine (0.02 g) and, after 30 minutes, 4-bromoanisole (11.69 g; 62.5 mmoles), in 1 hour, were added to the reaction mixture.

At the end of the addition, the reaction mixture was kept at 75° C. for 1 hour and, then, decanted obtaining a solution of 4-methoxyphenylmagnesiumbromide (solution A).

A mixture of 1-bromo-2,4-difluorobenzene (11.4 g; 59.1 mmoles), palladium chloride (0.00526 g; 0.0297 mmoles—Fluka) and triphenylphosphine (0.03088 g; 0.1177 mmoles—Fluka) was de-aerated by vacuum/nitrogen at 25° C. The mixture was heated at 85° C., kept under stirring for 15 minutes and, then, solution A was added in 3 hours. At the end of the addition, the reaction mixture was kept at 85° C. for 30 minutes.

After cooling at 60° C., a solution of 37% hydrochloric acid (2 ml) in water (10 ml) was added in 20 minutes.

The mixture was cooled at 40° C. and the phases were separated.

The solvent of the organic phase was evaporated under reduced pressure obtaining the desired compound (98.5% yield).

EXAMPLE 20

Preparation of 2,4-difluorophenylboronic acid

A) A 1M solution of 2,4-difluorophenylmagnesiumbromide in tetrahydrofuran (50 ml) was added dropwise to a solution of trimethylborate (5.71 g; 55 mmoles—Fluka) in tetrahydrofuran (42 g), cooled at −15° C. and under nitrogen.

At the end of the addition, the reaction mixture was heated at 20° C. in 30 minutes, poured into 2N hydrochloric acid (100 g) and, then, extracted with methylene chloride (2×50 g).

The collected organic phases were evaporated to dryness under reduced pressure. The resultant crude (6.78 g) was crystallized from water (60 ml) obtaining pure 2,4-difluorophenylboronic acid (5.91 g; 74.8% yield).

m.p. 240°–241° C.

$^1$H-NMR (300 MHz, CDCl$_3$): δ (ppm): 6.8 (m, 1H); 6.94 (m, 1H); 7.83 (m, 1H).

$^{19}$F-NMR (283.2 MHz, CDCl$_3$): δ (ppm, CF$_3$COOH): −107.25 (m, 1F); −105.7 (m, 1F).

B) Trimethylborate (25.98 g; 0.25 moles—Fluka) and a solution of 2,4-difluorophenylmagnesiumbromide (0.25 moles) in tetrahydrofuran (200 ml) were contemporaneously added, in 1 hour, into a reactor containing tetrahydrofuran (125 ml) under nitrogen while keeping the temperature at −15° C.

At the end of the addition, the reaction mixture was kept under stirring at −15° C. for 15 minutes.

After bringing the temperature to 0° C., water (17.5 ml) and 10% sulfuric acid (125 ml) were added in 10 minutes and in 15 minutes respectively.

After adding further water (250 ml) up to complete dissolution, the solution was extracted with ethyl ether (3×150 ml). The collected organic phases were evaporated to dryness obtaining a crude 2,4-difluorophenylboronic acid (36.98 g; titre 90%; 84.3% yield) which was used in the subsequent cross-coupling reaction without any further purification.

EXAMPLE 21

Preparation of 4-(2,4-difluorophenyl)-anisole from 2,4-difluorophenylboronic acid and palladium tetrakis(triphenylphosphine) (2%)

2,4-Difluorophenylboronic acid (1.00 g; 6.33 mmoles), prepared as described in example 20, and ethanol (2.5 g) were added to a mixture of palladium tetrakis(triphenylphosphine) (0.15 g; 0.13 mmoles), prepared from PdCl$_2$ (Fluka) and triphenylphosphine (Fluka), toluene (10 g), 4-bromoanisole (1.18 g; 6.30 mmoles) and a 2M aqueous sodium carbonate solution (6.3 g) kept under stirring at 20° C. and under nitrogen.

The reaction mixture was heated under reflux and stirring for 9 hours.

The reaction mixture, then, cooled at 20° C. in 1 hour and poured into a mixture of toluene (12 g) and water (9 g).

The organic phase was evaporated to dryness under reduced pressure obtaining the desired compound (1.58 g; titre 84.16%; 95% yield).

EXAMPLE 22

Preparation of 4-(2,4-difluorophenyl)-phenol from 2,4-difluorophenylboronic acid and palladium on charcoal/triphenylphosphine A) 2,4-Difluorophenylboronic acid (1.10 g; 6.97 mmoles), prepared as described in example 20, and ethanol (3 ml) were added to a mixture of 5% palladium on charcoal (0.067 g; 0.0315 mmoles), toluene (12 ml), triphenylphosphine (0.033 g; 0.126 mmoles), 4-bromophenol (1.09 g; 6.3 mmoles) and a 2M aqueous sodium carbonate solution (6 ml), kept under stirring at 20° C. and under nitrogen.

The reaction mixture was heated under reflux and stirring for 16 hours.

While keeping under reflux, 37% hydrochloric acid (1.7 ml) was added dropwise to the mixture.

The mixture was, then, filtered at warm by washing with warm acetone (2×10 ml).

The phases were separated and the aqueous phase was extracted with toluene (5 ml).

The toluene phase and the acetone phase were collected and the resultant organic solution was evaporated to dryness under reduced pressure.

The resultant crude (1.25 g; HPLC titre 75%) was purified by column chromatography (silica gel, toluene) obtaining the desired compound (0.9 g; 70% yield).

B) 2,4-Difluorophenylboronic acid (1.99 g; 12.6 mmoles), prepared as described in example 20, and ethanol (3 ml) were added to a mixture of 5% palladium on charcoal (0.0134 g; 0.0063 mmoles), toluene (12 ml), triphenylphosphine (0.0066 g; 0.0252 mmoles), 4-bromophenol (1.09 g; 6.3 mmoles) and a 2M aqueous sodium carbonate solution (6 ml), kept under stirring at 20° C. and under nitrogen.

The reaction mixture was heated under reflux and stirring for 20 hours.

While keeping at 60° C., 37% hydrochloric acid (1.7 ml) was added dropwise to the reaction mixture.

The mixture was filtered at 50° C. by washing with acetone (2×10 ml) at 50° C.

After separation of the phases, the aqueous phase was washed with toluene (5 ml).

The collected organic phases were evaporated to dryness under reduced pressure obtaining 4-(2,4-difluorophenyl)-phenol (1.34 g; titre 87%; 90% yield).

C) 2,4-Difluorophenylboronic acid (1.1 g; 6.97 mmoles), prepared as described in example 20, and ethanol (3 ml) were added to a mixture of 5% palladium on charcoal (0.0134 g; 0.0063 mmoles), toluene (12 ml), triphenylphosphine (0.0066 g; 0.0252 mmoles), 4-bromophenol (1.09 g; 6.3 mmoles) and a 2M aqueous sodium carbonate solution (6 ml), kept under stirring at 20° C. and under nitrogen.

The reaction mixture was heated under reflux and stirring for 20 hours.

While keeping at 60° C., 37% hydrochloric acid (1.7 ml) was added dropwise to the reaction mixture.

The mixture was filtered at 50° C. by washing with acetone (2×10 ml) at 50° C.

After separation of the phases, the aqueous phase was washed with toluene (5 ml).

The collected organic phases were evaporated to dryness under reduced pressure obtaining 4-(2,4-difluorophenyl)-phenol (1.25 g; titre 81%; 78% yield).

EXAMPLE 23

Preparation of 5-(2,4-difluorophenyl)-salicyclic acid from 2,4-difluorophenylboronic acid and palladium tetrakis(triphenylphosphine)

A) A mixture of 2,4-difluorophenylboronic acid (1 g; 6.3 mmoles), prepared as described in example 20, 5-bromosalicyclic acid (1.37 g; 6.3 mmoles), toluene (4 ml), ethanol (1 ml), 2M aqueous sodium carbonate solution (6 ml), palladium tetrakis(triphenylphosphine) (0.0366 g; 0.0316 mmoles), prepared form PdCl$_2$ (Fluka) and triphenylphosphine (Fluka), and benzyltrimethylammoniumbromide (0.0725 g; 0.3 mmoles) was heated under reflux and stirring for 10 hours.

Then, the reaction mixture was poured into 2N hydrochloric acid (50 ml) and toluene (40 ml) and acetone (10 ml) were added.

The mixture was heated at 65° C. and the phases were separated at warm.

After drying, the organic phase wasevaporated to dryness under reduced pressure. The resultant crude (1.66 g; HPLC titre 58%) was purified by column chromatography (silica gel, toluene:acetone:acetic acid=8:3:0.15) obtaining the desired compound (0.95 g; 60% yield).

B) A mixture of 5-bromosalicyclic acid (3 g; 13.8 mmoles), ethanol (2.3 ml), a 2M aqueous sodium carbonate solution (21 ml) and palladium tetrakis(triphenylphosphine) (0.073 g; 0.063 mmoles), prepared from PdCl$_2$ (Fluka) and triphenylphosphine (Fluka), was heated at 80° C. In 10 minutes, a solution of 2,4-difluorophenyl-boronic acid (2.75 g; titre 94%; 16.4 mmoles), prepared as described in example 20, in ethanol (3.2 ml) was added.

At the end of the addition, the reaction mixture was kept under stirring at 80° C. for 3 hours.

The resultant suspension was filtered obtaining 5(2,4-difluorophenyl)-salicyclic acid (2.8 g; titre 86%; 70% yield).

C) By working as described in example 23(B) but substituting ethanol with water, similar results were obtained.

What we claim is:

1. A process for the preparation of a biphenyl derivative of formula

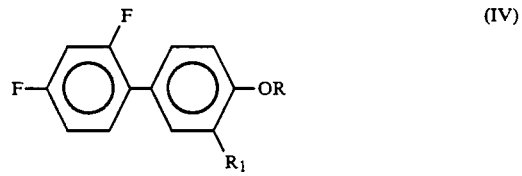

comprising the reaction between a difluorophenyl organometallic derivative of formula

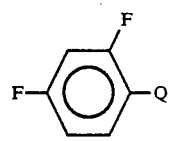

and a phenol compound of formula

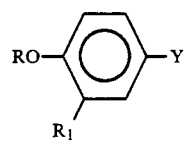

or the reaction between a phenol organometallic derivative of formula

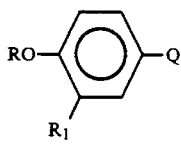

and a difluorophenyl compound of formula

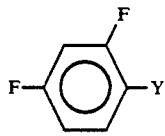

wherein Q is a copper atom or an $MX_n$ group where M is a metal selected from the group consisting of Mg, Zn, Cd, Hg, B and Al
- with the proviso when M is Mg, Zn, Cd or Hg, X is Cl, Br or I and n is 1; when M is B, X is Cl, Br, I, OH, a $C_{1-3}$ alkoxy and n is 2; when M is Al, X is $C_{1-4}$ alkyl and n is 2;
- Y is selected from the group consisting of Cl, Br, I and a trifluoromethanesulfonyloxy group;
- wherein R is selected from the group consisting of a hydrogen atom, a linear or branched $C_{1-5}$ alkyl, phenyl, substituted phenyl and benzyl; $R_1$ is selected from the group consisting of a hydrogen atom, a carboxyl group and a carboxyl precursor group;
- in the presence of a zero valent transition-metal based catalyst.

2. The process of claim 1, wherein said zero valent transition-metal based catalyst is selected from the group consisting of Pd and Ni, optionally supported, in the presence of ligands.

3. The process of claim 1, wherein said zero valent transition-metal based catalyst is prepared in situ, started from a salt selected from the group consisting of $NiCl_2$, $CoCl_2$, Nickel acetylacetonate, $FeCl_3$, $PdCl_2$, $Li_2CuCl_4$, palladium acetate and palladium acetylacetonate.

4. The process of claim 1, wherein said zero valent transition metal base catalyst is selected from the group consisting of palladium tetrakis(triphenylphosphine), nickel tetrakis(triphenylphosphine) and palladium on charcoal in the presence of triphenylphosphine.

5. The process of claim 1, wherein Q is $MX_n$, wherein M is Mg, X is Cl, Br or I, n is 1;
- Y is Cl, Br, I or a trifluoromethanesulfonyloxy group; and
- said zero valent transition-metal based catalyst is palladium tetrakis(triphenylphosphine) or nickel tetrakis(triphenylphosphine).

6. The process of claim 1, wherein Q is $MX_n$, wherein M is B, X is OH, n is 2;
- Y is Cl, Br, I or a trifluoromethanesulfonyloxy group; and
- said zero valent transition-metal based catalyst is palladium tetrakis(triphenylphosphine), nickel tetrakis(triphenylphosphine) or palladium on charcoal in the presence of triphenylphosphine.

7. A process for the preparation of 5-(2,4-difluorophenyl)-salicylic acid comprising:
i) reacting a difluorophenyl organometallic derivative of formula

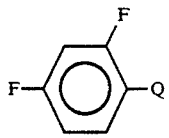

and a phenyl compound of formula

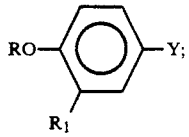

or reacting a phenyl organometallic derivative of formula

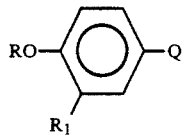

and a difluorophenyl compound of formula

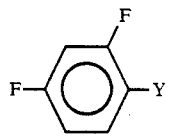

wherein Q is a copper atom or an $MX_n$ group where M is a metal selected from the group consisting of Mg, Zn, Cd, Hg, B and Al
- with the proviso when M is Mg, Zn, Cd or Hg, X is Cl, Br or I and n is 1; when M is B, X is Cl, Br, I or OH, a $C_{1-3}$ alkoxy and n is 2; when M is Al, X is $C_{1-4}$ alkyl and n is 2;
- Y is selected from the group consisting of Cl, Br, I or a trifluoromethanesulfonyloxy group;
- wherein R is selected from the group consisting of a hydrogen atom, a linear or branched $C_{1-5}$ alkyl, phenyl, substituted phenyl or benzyl; $R_1$ is selected from the group consisting of a hydrogen atom, a carboxyl group and a carboxyl precursor group;
- in the presence of a zero valent transition-metal based catalyst;
- ii) hydrolyzing the —OR ether group when $R_1 \neq H$; and
- iii) carboxylating the $R_1$ group when $R_1 = H$.

8. The process of claim 7, wherein said zero valent transition-metal based catalyst is selected from the group consisting of Pd and Ni, optionally supported, in the presence of ligands.

9. The process of claim 7, wherein said zero valent transition-metal based catalyst is prepared in situ, started from a salt selected from the group consisting of $NiCl_2$, $CoCl_2$, Nickel acetylacetonate, $FeCl_3$, $PdCl_2$, $Li_2CuCl_4$, palladium acetate and palladium acetylacetonate.

10. The process of claim 7, wherein said zero valent transition metal base catalyst is selected from the group consisting of palladium tetrakis(triphenylphosphine), nickel tetrakis(triphenylphosphine) and palladium on charcoal in the presence of triphenylphosphine.

11. The process of claim 7, wherein Q is $MX_n$, wherein M is Mg, X is Cl, Br, or I, n is 1;

Y is Cl, Br, I or a trifluoromethanesulfonyloxy group; and said zero valent transition-metal based catalyst is palladium tetrakis(triphenylphosphine) or nickel tetrakis(triphenylphosphine).

12. The process of claim 7, wherein Q is $MX_n$, wherein M is B, X is OH, n is 2;

Y is Cl, Br, I or a trifluoromethanesulfonyloxy group; and said zero valent transition-metal based catalyst is palladium tetrakis(triphenylphosphine), nickel tetrakis(triphenylphosphine), or palladium on charcoal in the presence of triphenylphosphine.

* * * * *